United States Patent [19]

Huff et al.

[11] 4,302,455

[45] Nov. 24, 1981

[54] 2-(4-AMINOPIPERIDINO)PYRAZINES

[75] Inventors: Joel R. Huff, Gwynedd; Stella W. King; Walfred S. Saari, both of Lansdale, all of Pa.

[73] Assignee: Merck & Co., Inc., Rahway, N.J.

[21] Appl. No.: 140,377

[22] Filed: Apr. 14, 1980

[51] Int. Cl.³ .................. A61K 31/495; C07D 401/04; C07D 401/14
[52] U.S. Cl. .................................. 424/250; 544/336; 544/357; 544/408; 544/409
[58] Field of Search ............... 544/357, 408, 409, 336; 424/250

[56] References Cited

PUBLICATIONS

Bayer; Methoden der Organischen Chemie (Houben-Weyl), Band VII/2b, 1976, pp. 1948-1952.
Derwent Abstracts, 02595D/03 (Abstract of EP publication 21973, 1/7/81.

*Primary Examiner*—Donald G. Daus
*Assistant Examiner*—James H. Turnipseed
*Attorney, Agent, or Firm*—William H. Nicholson; Mario A. Monaco

[57] ABSTRACT

2-(4-Aminopiperidino)pyrazines are useful as analgesic and antidepressant agents. They are prepared by reductive amination of the corresponding 2-(4-oxopiperidino)pyrazines.

9 Claims, No Drawings

2-(4-AMINOPIPERIDINO)PYRAZINES

BACKGROUND OF THE INVENTION

This invention relates to 2-(4-aminopiperidino)pyrazines and derivatives thereof which are useful as analgesic and antidepressant agents.

There are many structurally related compounds known in the art, and known to have biological activity. For example piperazinyl-pyrazines are known in U.S. Pat. Nos. 4,081,542 and 4,082,844 to have anorexic, antidepressant, antihypertensive, analgesic and sleep inducing agents. Similarly, piperazinyl-pyridines (U.S. Pat. No. 4,078,063); 3-(1-piperazinyl)pyrido[2,3-b]pyrazines (U.S. Pat. No. 4,082,845); 6-(1-piperazinyl)quinoxalines (U.S. Pat. No. 4,091,101) and 2-(1-piperazinyl)-quinoxalines (British Patent No. 1,440,722) are also described as anorexic, antidepressant, antihypertensive, analgesic and sleep inducing agents.

Now with this invention there is provided a group of novel compounds which are 2-(4-aminopiperidino)-pyrazines which are useful as analgesic and antidepressant agents by virtue of their serotoninergic properties.

It is also an object of this invention to provide novel processes for the preparation of the novel compounds of this invention; novel pharmaceutical formulations comprising these compounds as active ingredient; and a novel method of treating pain and depression by administration, to a patient, of one of the novel compounds or pharmaceutical formulation thereof.

DETAILED DESCRIPTION OF THE INVENTION

The novel compounds of this invention have structural formula:

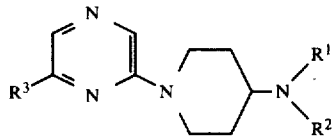

or a pharmaceutically acceptable salt thereof, wherein $R^1$ is hydrogen or $C_{1-3}$ alkyl; $R^2$ is hydrogen, $C_{1-3}$ alkyl or

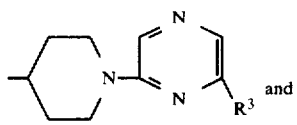
and $R^3$ is halo, such as chloro, bromo, fluoro or iodo, trifluoromethyl, $C_{1-3}$ alkyl, $C_{1-3}$ alkoxy, $C_{1-3}$ alkylthio, phenoxy, phenylthio, di($C_{1-3}$ alkyl)amino or phenyl.

It is preferred that $R^1$ be hydrogen and $R^2$ be hydrogen or

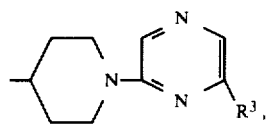, and that $R^3$ be halo, especially chloro.

The novel process for preparing the compounds of this invention comprises mixing together a 6-$R^3$-2-(4-oxo-1-piperidyl)pyrazine and an amine of formula $NR^1R^2$ in a protic solvent such as a lower alkanol, preferably methanol in the presence of ammonium acetate and sodium cyanoborohydride. Temperatures between about 15° C. and 35° C. may be employed, preferably about 20°-25° C. or room temperature. The mixing is continued until reaction is substantially complete and requires about 40 to about 100 hours, usually about 60 hours at room temperature.

In the absence of any added amine, the product is the dimer, that is $R^1$ is hydrogen and $R^2$ is

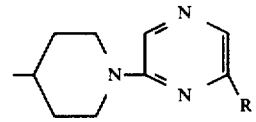

which is formed from further reaction of an oxo group with the amino compound initially formed from reductive amination of the oxo group with ammonium acetate and sodium cyanoborohydride.

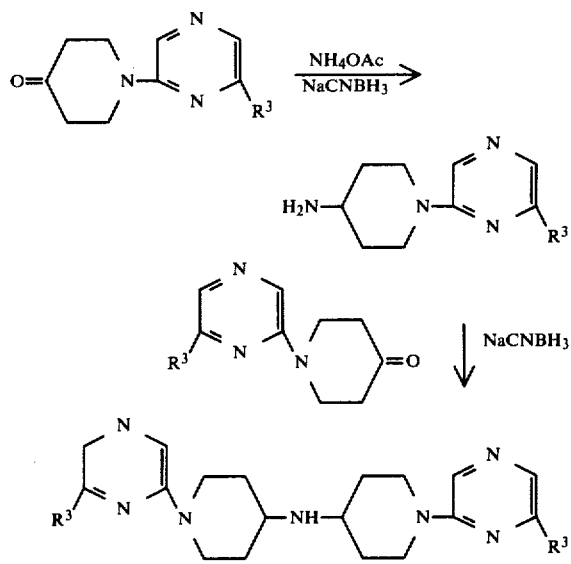

In the presence of a large excess of an added amine, such as ammonia, formation of the simpler 4-amino product is favored.

The compounds active in the novel method of treatment of this invention may be administered as analgesic or antidepressant agents to mammalian species, in amounts ranging from about 0.01 to about 20 mg per kg of body weight, preferably from about 0.05 to about 5 mg per kg of body weight in a single dose or in 2 to 4 divided doses.

These compounds in the described dosages may be administered orally; however, other routes such as intraperitoneally, subcutaneously, intramuscularly, or intravenously may be employed.

The active compounds of the present invention are administered orally, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. The amount of active compound in such therapeutically useful compositions or preparations is such that a suitable dosage will be obtained.

The tablets, troches, pills, capsules, and the like, may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate, and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coating or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylio, succinic acid, theophylline, 8-chlorotheophylline, p-aminobenzoic, p-acetamidobenzoic, or methanesulfonic.

EXAMPLE 1

6-Chloro-2-(4-aminopiperidino)pyrazine hydrochloride

Step A: Preparation of 6-chloro-2-(4-oxopiperidino)-pyrazine

A solution of 3.0 g (20 mmol) 2,6-dichloropyrazine, 2.0 g (20 mmol) triethylamine, and 2.9 g (20 mmol) 1,4-dioxa-8-azaspiro[4.5]decane in 60 ml acetonitrile is refluxed 17 hours. The solvent is removed in vacuo, and the residue is dissolved in ethylacetate. After washing with water and brine, the organic fraction is dried (MgSO4) and evaporated to an oil. The oil is dissolved in 30 ml acetone and mixed with 30 ml 1N HCl. After heating this solution on the steam bath 30 minutes, the acetone is evaporated, and the concentrate is cooled to 10° C. A solid separates which is filtered and dried to afford 3 g (71%) of the desired product.

Step B: Preparation of 6-chloro-2-(4-aminopiperidino)pyrazine hydrochloride

To a solution of 17.1 g (81 mmol) 6-chloro-2-(4-oxopiperidino)pyrazine in 250 ml methanol which has been saturated with gaseous NH3 is added 62.4 g (0.81 mol) NH4OAc and 5.0 g (80 mmol) NaCNBH3. After stirring at 20°-25° C. for 60 hours, the MeOH is removed in vacuo. Water is added to the residue, and the pH is adjusted to 14. The product is extracted into ethyl acetate which is dried and concentrated. Chromatography of the residue over silica gel, eluting with 5% MeOH/CHCl3 saturated with NH3, gives the product base which is converted to the hydrochloride salt with ethanolic HCl. Recrystallization from water/acetone affords the desired product, m.p. 291° C. (dec.).

Employing the procedure substantially as described in Example 1, Steps A and B but optionally substituting for the 2,6-dichloropyrazine used in Step A thereof a 6-$R^3$-2-chloropyrazine and optionally substituting for the ammonia used in Step B an amine of formula $HNR^1R^2$ there are produced the aminopiperidinopyrazines described in Table I, in accordance with the following reaction scheme:

TABLE I

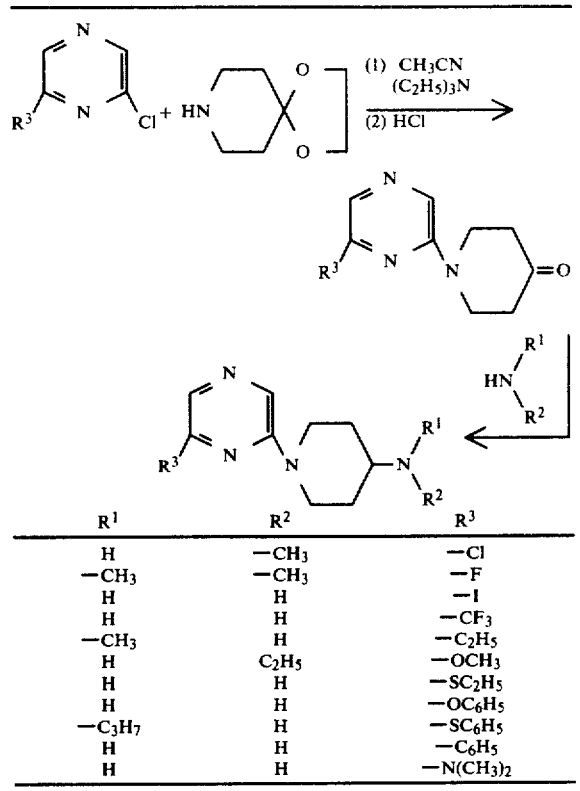

| $R^1$ | $R^2$ | $R^3$ |
|---|---|---|
| H | —CH3 | —Cl |
| —CH3 | —CH3 | —F |
| H | H | —I |
| H | H | —CF3 |
| —CH3 | H | —C2H5 |
| H | C2H5 | —OCH3 |
| H | H | —SC2H5 |
| H | H | —OC6H5 |
| —C3H7 | H | —SC6H5 |
| H | H | —C6H5 |
| H | H | —N(CH3)2 |

EXAMPLE 2

Bis4-[1-(6-chloro-2-pyrazinyl)piperidinyl]amine

A mixture of 7.5 g (35 mmol) 6-chloro-2-(4-oxopiperidino)pyrazine, 27.5 g (0.36 mol) NH4OAc, and 1.68 g (27 mmol) NaCNBH3 in 100 ml methanol is stirred at 20°-25° for 60 hours. Methanol is removed in vacuo, and the residue is partitioned between EtOAc and H2O. The organic layer is separated and washed with water and brine, whereupon a precipitate forms. The solid is filtered and triturated with boiling MeOH. It is then chromatographed over silica gel, eluting with chloroform saturated with NH3. Recrystallization from chloroform/petroleum ether affords the product, m.p. 142°-44° C.

EXAMPLE 3

| Preparation of Capsule Formulation | |
|---|---|
| Ingredient | Milligrams per Tablet |
| 6-Chloro-2-(4-aminopiperidino)-pyrazine hydrochloride | 6 |
| Starch | 87 |

-continued

| Preparation of Capsule Formulation | |
|---|---|
| Ingredient | Milligrams per Tablet |
| Magnesium stearate | 7 |

The active ingredient, starch and magnesium stearate are blended together. The mixture is used to fill hard shell capsules of a suitable size at a fill weight of 100 milligrams per capsule.

EXAMPLE 4

| Preparation of Tablet Formulation | |
|---|---|
| Ingredient | Milligrams per Tablet |
| Bis-4-[1-(6-chloro-2-pyrazinyl)-piperidinyl]amine | 12 |
| Lactose | 200 |
| Corn starch (for mix) | 50 |
| Corn starch (for paste) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 12 milligrams of active ingredient.

EXAMPLE 5

| Preparation of Oral Syrup Formulation | |
|---|---|
| Ingredient | Amount |
| 6-Chloro-2-(4-aminopiperidino)-pyrazine hydrochloride | 25 mg |
| Sorbitol solution (70% N.F.) | 40 ml |
| Sodium benzoate | 150 mg |
| Sucaryl | 90 mg |
| Saccharin | 10 mg |
| Cherry Flavor | 50 mg |
| Distilled water qs to | 100 ml |

The sorbitol solution is added to 40 milliliters of distilled water and the active ingredient is suspended therein. The sucaryl, saccharin, sodium benzoate, flavor and dye are added and dissolved in the above solution. The volume is adjusted to 100 milliliters with distilled water.

Other ingredients may replace those listed in the above formulation. For example, a suspending agent such as bentonite magma, tragacanth, carboxymethylcellulose, or methylcellulose may be used. Phosphates, citrates or tartrates may be added as buffers. Preservatives may include the parabens, sorbic acid and the like and other flavors and dyes may be used in place of those listed above.

What is claimed is:

1. A compound of structural formula:

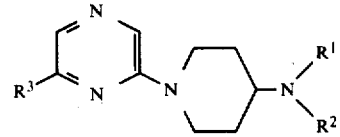

or a pharmaceutically acceptable salt thereof, wherein $R^1$ is hydrogen or $C_{1-3}$ alkyl; $R^2$ is hydrogen, $C_{1-3}$ alkyl, or

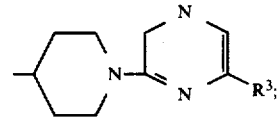

and $R^3$ is halo, trifluoromethyl, $C_{1-3}$ alkyl, $C_{1-3}$ alkoxy, $C_{1-3}$ alkylthio, phenoxy, phenylthio, di($C_{1-3}$ alkyl)amino or phenyl.

2. The compound of claim 1, wherein $R^3$ is halo, $R^1$ is hydrogen and $R^2$ is hydrogen or

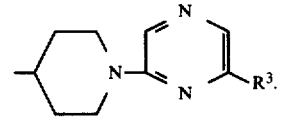

3. The compound of claim 2, wherein $R^3$ is chloro and $R^1$ and $R^2$ are hydrogen.

4. An analgesic, antidepressant, pharmaceutical composition comprising a pharmaceutical carrier and an analgesic, antidepressant effective amount of a compound of structural formula:

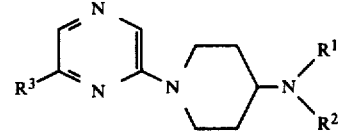

or a pharmaceutically acceptable salt thereof, wherein $R^1$ is hydrogen or $C_{1-3}$ alkyl; $R^2$ is hydrogen, $C_{1-3}$ alkyl, or

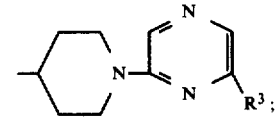

and $R^3$ is halo, trifluoromethyl, $C_{1-3}$ alkyl, $C_{1-3}$ alkoxy, $C_{1-3}$ alkylthio, phenoxy, phenylthio, di($C_{1-3}$ alkyl)amino or phenyl.

5. The composition of claim 4, wherein $R^3$ is halo, $R^1$ is hydrogen and $R^2$ is hydrogen or

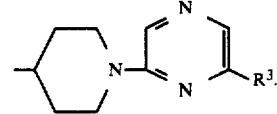

6. The composition of claim 5, wherein $R^3$ is chloro, and $R^1$ and $R^2$ are hydrogen.

7. A method of treating pain or depression which comprises the administration to a patient in need of such treatment an analgesic, antidepressant effective amount of a compound of structural formula:

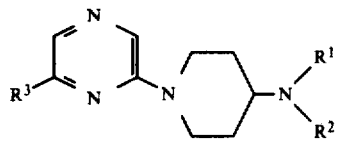

or a pharmaceutically acceptable salt thereof, wherein $R^1$ is hydrogen or $C_{1-3}$ alkyl; $R^2$ is hydrogen, $C_{1-3}$ alkyl, or

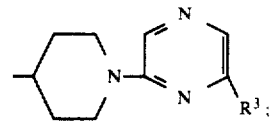

and $R^3$ is halo, trifluoromethyl, $C_{1-3}$ alkyl, $C_{1-3}$ alkoxy, $C_{1-3}$ alkylthio, phenoxy, phenylthio, di($C_{1-3}$ alkyl)amino or phenyl.

8. The method of claim 7, wherein $R^3$ is halo, $R^1$ is hydrogen and $R^2$ is hydrogen or

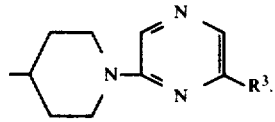

9. The method of claim 8, wherein $R^3$ is chloro, and $R^1$ and $R^2$ are hydrogen.

* * * * *